United States Patent
Schlegel et al.

(10) Patent No.: US 6,191,295 B1
(45) Date of Patent: Feb. 20, 2001

(54) STABLE TRIMERIC ISOPROPOXYALANE, METHOD OF PRODUCING THE SAME, AND USE THEREOF

(75) Inventors: Andreas Schlegel, Munich; Heinrich Noeth, Gruenwald; Peter Rittmeyer, Sulzbach; Dieter Hauk, Friedberg-Fauerbach; Ulrich Wietelmann, Friedrichsdorf, all of (DE)

(73) Assignee: Metallgesellschaft Aktiengesellschaft, Frankfurt am Main (DE)

( * ) Notice: Under 35 U.S.C. 154(b), the term of this patent shall be extended for 0 days.

(21) Appl. No.: 09/423,595

(22) PCT Filed: May 7, 1998

(86) PCT No.: PCT/EP98/02693

§ 371 Date: Jan. 12, 2000

§ 102(e) Date: Jan. 12, 2000

(87) PCT Pub. No.: WO98/51691

PCT Pub. Date: Nov. 19, 1998

(30) Foreign Application Priority Data

May 13, 1997 (DE) .............................................. 197 19 809

(51) Int. Cl.$^7$ ........................................................ C07F 5/06
(52) U.S. Cl. ............................................. 556/178; 556/187
(58) Field of Search ...................................... 556/178, 187

(56) References Cited

FOREIGN PATENT DOCUMENTS 19529241    2/1997   (DE) .

OTHER PUBLICATIONS

H. Noth, et al.,$^7$ Uber Alkoxyalane und Alkoxyaluminum–boranate Bd. 368, Nr. 1–2, Apr. 1968.

Primary Examiner—Porfirio Nazario-Gonzalez
(74) Attorney, Agent, or Firm—Fulbright & Jaworski, LLP

(57) ABSTRACT

The invention relates to stable trimer isopropoxyalane of composition $H_5Al_3(OiPr)_4$, wherein iPr is a $(CH_3)_2CH$ radical. The invention also relates to a method for producing stable trimer isopropoxyalane, wherein $AlH_3$ is reacted with $Al(OiPr)_3$ or isopropanol in a molar ratio of 5:4 or 3:4 in a solvent or solvent mixture. The stable trimer isopropoxyalane is particularly suitable for use as a reducing agent in organic and inorganic synthesis, as a source for aluminium or aluminium oxide in the electronics or ceramics industry or to produce pigments.

11 Claims, No Drawings

STABLE TRIMERIC ISOPROPOXYALANE, METHOD OF PRODUCING THE SAME, AND USE THEREOF

DESCRIPTION

This invention relates to a stable trimeric isopropoxyalane, to a method of producing the stable trimeric isopropoxyalane, and to the use thereof.

Aluminium hydride ($AlH_3$, alane) and complex metal aluminium hydrides (alanates) are commonly used, strong reducing agents. They are therefore used for reducing carbonyl compounds, esters and nitro compounds. The high reactivity with respect to most functional groups, which is desired on the one hand, in some cases leads to problems due to the lack of selectivity of the reducing agents on the other hand. This is the case for instance when one molecule includes several reducible functional groups, or when the reducing agents not only act as hydrogen donor, but also as base. The partial replacement of the hydrogen in the aluminium hydride and/or in the complex metal aluminium hydrides by suitable substituents leads to a variation of the reduction properties and the basicity of the reducing agents. There is mostly employed the introduction of alkoxy substituents into aluminium hydride and/or into the complex metal aluminium hydrides. For instance, the reactivity of the hydrogen in the lithium-tri(t-butoxy)aluminium hydride is diminished due to the steric shielding to such an extent that under certain conditions carboxylic acid derivatives are only reduced to the aldehyde.

A plurality of alkoxy-substituted aluminium hydrides of the type $MH_xAl(OR)_{4-x}$ and $H_yAl(OR)_{3-y}$ (x=1–3, y=1–2, R=organic residue) are known. Of these, merely $NaH_2Al(OCH_2CH_2OCH_3)_2$ is of economic importance. This alanate, however, has the disadvantage of a relatively low hydride-hydrogen content (<1 wt-%), which leads to the fact that when using this alanate for reduction reactions a relatively large amount is required and a correspondingly large amount of waste products is obtained. Above all, however, the byproduct methoxyethanol, which is necessarily produced in the hydrolysis of this alanate, is extremely toxic.

The mono- and dialkoxyalanes produced from unbranched alcohols are completely insoluble in aprotic solvents due to their polymeric structure and can therefore not be used for reduction purposes. The tendency to polymerisation can be suppressed in that the steric space filling of the alkoxy residue is increased. For instance, the mono- and di-tert-butoxyalanes are very easily soluble in the commonly used organic solvents. Tert-butoxyalanes can, however, not economically be produced in every case, as the aluminium alkoxide required for the reaction in accordance with the equation $(3-x)Al(OtBu)_3 + xAlH_3 \rightarrow 3H_xAl(OtBu)_{3-x}$, (x=1,2) is difficult to prepare and/or not commercially available.

From DE-OS 195 29 241 alkoxyalanes of the general formula $Al(OR)_aH_b$ are known, where R is an alkyl residue with 3 to 10 C atoms or a cycloalkyl residue with 5 to 8 C atoms, where the residues R can be the same or different, where a is 1 or 2, b is 1 or 2, and the sum a+b=3. From the reference it can be taken that the alkoxyalanes described there are present in dimeric form. Corresponding to the reference, the known dimeric alkoxyalanes can also include propyl and/or isopropyl residues as residues R. For producing the known alkoxyalanes, the DE-OS 195 29 241 proposes a method wherein $AlH_3$ is reacted with an alcohol ROH in the presence of an inert organic solvent, where the molar ratio is either substantially 1:1 or substantially 1:2. According to this method, there is then formed either $H_2AlOR$ or $HAl(OR)_2$, where these alkoxyalanes are present as dimers. The alkoxyalanes known from DE-OS 195 29 241 should be used for producing optically variable systems.

Isopropoxyalanes are known for about 30 years. They can be produced by reacting aluminium hydride ($AlH_3$) with isopropanol in a molar ratio of 2:1 or 1:1, or by reacting $AlH_3$ with aluminium isopropoxide. As regards the properties of the isopropoxy-substituted alanes contradictory statements were made, as depending on the conditions of preparation different oligomers are quite obviously obtained. The different statements concerning the properties of the isopropoxy-substituted alanes probably result from the fact that the known isopropoxyalanes of the stoichiometry $H_2Al(OiPr)$ and $HAl(OiPr)_2$ have no dissociative stability and/or are not pure. By means of so far not published examinations it was demonstrated that these two compounds are capable of disproportionation. The disproportionation reactions lead to a change in the product composition due to precipitation and consecutive reactions, so that reduction-active compounds of very different reactivity are present at the same time, which prevents a high chemoselectivity. Therefore, the two aforementioned compounds can not even be produced and supplied in the form of stable, salable solutions.

The publication of Nöth and Suchy, Zeitschrift für anorganische und allgemeine Chemie, Vol. 358, 1968, pages 44 to 66, describes the reactions of $AlH_3$ with isopropanol in a molar ratio of 1:1 and 1:2. The publication comes to the conclusion that the reaction of $AlH_3$ with isopropanol in a molar ratio of 1:1 does either not take place quantitatively, so that unreacted $AlH_3$ remains in the reaction solution and the $H_2AlOiPr$ formed furthermore reacts with isopropanol to form $HAl(OiPr)_2$, or that the $H_2AlOiPr$ develops the following equilibrium:

$2H_2AlOiPr \rightleftharpoons HAl(OiPr)_2 + AlH_3$

From the reaction solution, the dimeric isopropoxyalane $(H_2AlOiPr)_2$ could, however, be isolated. According to the publication, during the reaction of $AlH_3$ with isopropanol in a molar ratio of 1:2 the $HAl(OiPr)_2$ is formed, which is in equilibrium with the mono- and triisopropoxyalane, which, however, promotes the formation of the diisopropoxyalane. $2HAl(OiPr)_2 \rightleftharpoons Al(OiPr)_3 + H_2AlOiPr$ The diisopropoxyalane is dissolved in benzene for instance in a trimeric form and therefore has the composition $H_3Al_3(OiPr)_6$. However, the aforementioned disproportionation equilibrium develops slowly in the solution of the trimeric diisopropoxyalane, so that the composition of the solution is changed in a disadvantageous way.

It is the object underlying the invention to create a chemoselective, stable isopropoxyalane, which is easily soluble in commonly used solvents, whose solutions are stable in storage, which has an increased hydride content as compared to available alkoxyalanes, which forms no toxic byproducts during hydrolysis, and which can be prepared from inexpensive as well as available raw materials.

The object underlying the invention is solved by creating the stable trimeric isopropoxyalane of the composition $H_5Al_3(OiPr)_4$, where iPr is a $(CH_3)_2CH$ residue. It was surprisingly found out that this trimeric form of the isopropoxyalane has a high stability; it melts at about 60° C., can be sublimated at 40° C./0.5 mbar, be prepared in pure form by sublimation and be characterized unambiguously by means of spectroscopy ($^{27}Al$-NMR, $C_6D_6$:δ=125 ppm, 60 ppm; $^1H$-NMR, $C_6D_6$:δ=1.26 ppm, d24H and 4.18 ppm, sep 4H). The stable trimeric isopropoxyalane has the structural formula

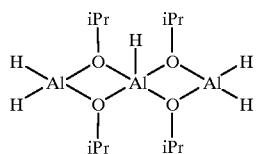

The molar mass corresponds to the structural formula. In contrast to the alanes $H_2AlOiPr$ and $HAl(OiPr)_2$, the trimeric isopropoxyalane in accordance with the invention does not disproportionate, but it is very stable and can therefore be stored in solid or in particular in dissolved form also for an extended period and is therefore available as a salable reducing agent.

In accordance with the invention it is furthermore provided that the stable trimeric isopropoxyalane is dissolved in a solvent or solvent mixture in a concentration of 20 to 80 wt-%, where as solvent there are used ethers, tertiary amines, alkyl phosphates, aromatic hydrocarbons, saturated aliphatic hydrocarbons or mixtures of these solvents. In dissolved form, the trimeric isopropoxyalane is very stable, and therefore these solutions are particularly suited as salable product.

It is particularly advantageous when the trimeric isopropoxyalane is dissolved in diethyl ether, tetrahydrofuran, ethylene glycol dimethyl ether, triethylamine, toluene, hexane, cyclohexane and/or methylcyclohexane, as the aforementioned solvents are easly available, easy to handle as well as inexpensive, and as the trimeric isopropoxyalane is particularly stable in these solvents. At 20° C., the solubility of the trimeric isopropoxyalane is about 45 wt-% in toluene, about 30 wt-% in hexane, and about 50 wt-% in tetrahydrofuran, where the salable solutions have an isopropoxyalane content which is slightly below the maximum solubility.

The object underlying the invention is furthermore solved by creating a method of producing the trimeric isopropoxyalane, where $AlH_3$ is reacted with $Al(OiPr)_3$ or with isopropanol in a molar ratio of 5:4 or of 3:4 in a solvent or a solvent mixture. When using the respective molar ratio in accordance with the invention, the stable trimeric isopropoxyalane is obtained from the starting substances, and there is no formation of unstable reaction products. In addition, the solutions prepared in accordance with the inventive method can be sold directly without further cleaning, where the concentration of the trimeric isopropoxyalane in the salable solutions is quite high.

It was found out that the method in accordance with the invention can also be performed successfully when the molar ratio of $AlH_3$ to $Al(OiPr)_3$ or to isopropanol is 5:3.7 to 5:4.3 or 3:3.7 to 3:4.3. With this variation of the molar ratios of the starting substances, the stable trimeric isopropoxyalane is obtained as main product, and the alanes formed as byproducts disadvantageously influence the product quality only to a minor degree, which is still acceptable for industrial applications. The variation of the molar ratios within the inventive limits is important in particular for the execution of the method on a technical scale, as the starting substances frequently contain impurities which slightly change the molar ratio of the starting substances of 5:4 or 3:4, which should be achieved in accordance with the invention. However, this does not lead to a noticeable deterioration of the quality of the product obtained with this method.

The inventive method can advantageously be performed such that $AlH_3$ and $Al(OiPr)_3$ are reacted in accordance with the equation $5AlH_3+4Al(OiPr)_3\rightarrow 3H_5Al_3(OiPr)_4$ at a reaction temperature of −20 to +80° C., preferably −5 to +35° C. At the inventive reaction temperatures the solvents used are easy to handle, and the reaction rate is high enough.

The method in accordance with the invention can furthermore be performed such that $AlH_3$ and isopropanol are reacted in accordance with the equation

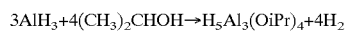

at a reaction temperature of −80 to +80° C. At the inventive reaction temperatures the reaction rate is high enough, and the solvents used are easy to handle.

In accordance with the invention it turned out to be particularly advantageous when the $AlH_3$ is used in the form of a Lewis base addition product, where as Lewis base there are used ethers or tertiary amines. As Lewis base there are used open-chain, cyclic or polyfunctional ethers, which can remain in the product solution. As amines there can be used in particular trialkyl amines $R_3N$, where R is an alkyl residue with 1 to 6 C atoms. The exact composition of the addition product consisting of $AlH_3$ and a Lewis base depends on the Lewis base used and on the production of the addition product and varies within wide limits. However, the addition product advantageously has a higher stability as compared to the pure $AlH_3$ and is easily soluble in many solvents as well as easily accessible.

As solvents for performing the inventive method there are used ethers, tertiary amines, alkylphosphanes, aromatic hydrocarbons, saturated aliphatic hydrocarbons or mixtures of these solvents. The solvents used must be liquid in a part of the temperature range from −80 to +100° C. and be available anhydrous.

The method in accordance with the invention can be performed particularly successfully when as solvent or solvent mixture there are used diethyl ether, tetrahydrofuran, ethylene glycol dimethyl ether, triethylamine, toluene, hexane, cyclohexane and/or methylcyclohexane. These solvents are inexpensive, easily available and can be dehydrated at reasonable costs and with commonly used methods.

In accordance with the invention, the stable trimeric isopropoxyalane is used as reducing agent in organic and inorganic syntheses, as a source for aluminium or aluminium oxide in the electronics and ceramics industry and for producing pigments, where for synthetic chemistry the use in the form of solutions is preferred. The production of aluminium, aluminium oxide and pigments from stable trimeric isopropoxyalane can for instance be effected according to the CVD method in a reducing or oxidizing atmosphere.

The subject-matter of the invention will subsequently be explained with reference to embodiments.

EXAMPLE 1

To a solution of 0.753 g (25 mmol) $AlH_3$ in 30 ml tetrahydrofuran a solution of 4.08 g (20 mmol) $Al(OiPr)_3$ in 15 ml tetrahydrofuran is added at 0° C. within 15 min. To complete the reaction, the mixture is stirred for one hour at room temperature. Subsequently, the solvent is distilled off at 20 mbar as well as 30° C., and the residue is then dried at 1 mbar and 20° C. Then, the stable trimeric isopropoxyalane formed is purified by sublimation at 0.5 mbar and 40° C. The yield is 4.35 g; this is 90% of the theoretical yield. The product has the aforementioned spectroscopic data.

EXAMPLE 2

To a suspension of 16.35 g LiH (2.06 mol) and 250 ml diethyl ether, a solution of 87.5 g (0.656 mol) $AlCl_3$ in 260 g diethyl ether is added dropwise within 4 hours. During this period, the reaction temperature is maintained at 0 to 5° C. According to the equation $15LiH+5\ AlCl_3 \rightarrow 5AlH_3+15LiCl$ aluminium hydride is formed, which is present in the solution as addition product with the Lewis base diethyl ether. Subsequently, 109 g (0.534 mol) $Al(OiPr)_3$ in solid form is introduced into the solution in portions at 0 to 5° C. The mixture is stirred for one hour at 5° C. and then heated to room temperature. After separating the LiCl by filtration, the diethyl ether is distilled off. Upon drying the product in a vacuum, a colorless oil is left, which slowly crystallizes. The yield of stable trimeric isopropoxyalane is 121.6 g; the crystalline product has the aforementioned spectroscopic data. The product contains 13.7 mmol H /g and 8.8 mmol Al/g. For the theoretical yield of 100% these values are 15.5 mmol $H^-$/g and 9.3 mmol Al/g.

EXAMPLE 3

To a solution of 3 g (100 mmol) $AlH_3$ in 100 ml diethyl ether there are slowly added 8 g (133 mmol) isopropanol, dissolved in 20 ml diethyl ether. Upon termination of the generation of hydrogen, the mixture is stirred for one hour at room temperature. Subsequently, the solution is processed corresponding to Example 1. The yield of trimeric isopropoxyalane is 10.1 g; this is 95% of the theoretical yield. This product has the aforementioned spectroscopic data.

What is claimed is:

1. A stable trimeric isopropoxyalane of the composition $H_5Al_3(OiPr)_4$, where iPr is a $(CH_3)_2CH$ residue.

2. The stable trimeric isopropoxyalane as claimed in claim 1, which is dissolved in a solvent or solvent mixture in a concentration of 20 to 80 wt-%, where as solvent there are used ethers, tertiary amines, alkylphosphanes, aromatic hydrocarbons, saturated aliphatic hydrocarbons or mixtures of these solvents.

3. The stable trimeric isopropoxyalane as claimed in claim 1, which is dissolved in diethyl ether, tetrahydrofuran, ethylene glycol dimethyl ether, triethylamine, toluene, hexane, cyclohexane and/or methylcyclohexane.

4. A method of producing the stable trimeric isopropoxyalane as claimed in claim 1, wherein $AlH_3$ is reacted with $Al(OiPr)_3$ or with isopropanol in a molar ratio of 5:4 or 3:4 in a solvent or a solvent mixture.

5. The method as claimed in claim 4, wherein the molar ratio of $AlH_3$ to $Al(OiPr)_3$ or to isopropanol is 5:3.7 to 5:4.3 or 3:3.7 to 3:4.3, respectively.

6. The method as claimed in claim 4, wherein $AlH_3$ and $Al(OiPr)_3$ are reacted according to the equation $5AlH_3+4Al(OiPr)_3 \rightarrow 3H_5Al_3(OiPr)_4$ at a reaction temperature of −20 to +80° C.

7. The method as claimed in claim 6, wherein the reaction temperature is −5 to +35° C.

8. The method as claimed in claim 4, wherein $AlH_3$ and isopropanol are reacted according to the equation $3AlH_3+4(CH_3)_2CHOH \rightarrow H_5Al_3(OiPr)_4+4H_2$ at a reaction temperature of −80 to +80° C.

9. The method as claimed in claim 4, wherein the $AlH_3$ is used in the form of a Lewis base addition product, where as Lewis base ethers or tertiary amines are used.

10. The method as claimed in claim 4, wherein as solvents there are used ethers, tertiary amines, alkylphosphanes, aromatic hydrocarbons, saturated aliphatic hydrocarbons or mixtures of these solvents.

11. The method as claimed in claim 4, wherein as solvent or solvent mixture there are used diethyl ether, tetrahydrofuran, ethylene glycol dimethyl ether, triethylamine, toluene, hexane, cyclohexane and/or methylcyclohexane.

* * * * *